(12) United States Patent
Helmer et al.

(10) Patent No.: US 12,346,491 B2
(45) Date of Patent: Jul. 1, 2025

(54) SYSTEM AND METHOD FOR PROVIDING ADDITIONAL INFORMATION TO A USER OF AN INJECTION DEVICE

(71) Applicant: Sanofi, Paris (FR)

(72) Inventors: Michael Helmer, Frankfurt am Main (DE); Martin Vitt, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 18/010,977

(22) PCT Filed: Jun. 23, 2021

(86) PCT No.: PCT/EP2021/067148
§ 371 (c)(1),
(2) Date: Dec. 16, 2022

(87) PCT Pub. No.: WO2021/260006
PCT Pub. Date: Dec. 30, 2021

(65) Prior Publication Data
US 2023/0229227 A1 Jul. 20, 2023

(30) Foreign Application Priority Data

Jun. 25, 2020 (EP) ..................................... 20315319

(51) Int. Cl.
*G06F 3/01* (2006.01)
*G06F 16/955* (2019.01)

(52) U.S. Cl.
CPC ............ *G06F 3/01* (2013.01); *G06F 16/9554* (2019.01)

(58) Field of Classification Search
CPC ...... G06F 3/01; G06F 16/9554; G06F 3/0304; G16H 20/17
See application file for complete search history.

(56) References Cited

U.S. PATENT DOCUMENTS 8,590,777 B1 * 11/2013 Roman ................. G06F 16/583
235/487
10,325,529 B1 * 6/2019 Kuhn .................... G09F 3/0297
(Continued)

FOREIGN PATENT DOCUMENTS

JP 2009-506395 A 2/2009
WO WO-0198169 A1 * 12/2001 ............. A61F 17/00
(Continued)

OTHER PUBLICATIONS

International Preliminary Report on Patentability in International Appln. No. PCT/EP2021/067148, mailed on Jan. 5, 2023, 13 pages.
(Continued)

*Primary Examiner* — Tuyen K Vo
(74) *Attorney, Agent, or Firm* — Fish & Richardson P.C.

(57) ABSTRACT

A system is provided for providing additional information to a user of an injection device, the system comprising an injection device, a user device and instructions for use of the injection device, the instructions for use comprising at least one tag, wherein the tag is associated with the instructions for use or with a section or a subsection of the instructions for use, wherein the memory of the user device stores instructions which, when executed by the processor, cause the user device to: scan, using a camera and/or a wireless module, the tag; identify the instructions for use or the section of the instructions for use which the tag is associated with; based on the identification, provide the user with additional information on the particular instructions for use or the particular section of the instructions for use.

6 Claims, 3 Drawing Sheets

(56) References Cited

U.S. PATENT DOCUMENTS

| | | | |
|---|---|---|---|
| 2002/0008047 A1* | 1/2002 | Hammond | A61F 17/00 206/570 |
| 2006/0275064 A1* | 12/2006 | Minari | G03G 21/04 399/366 |
| 2007/0095707 A1* | 5/2007 | Yahiel | B65D 23/14 206/459.5 |
| 2007/0194128 A1* | 8/2007 | Coe | A45C 11/18 235/486 |
| 2011/0205029 A1* | 8/2011 | Sanvincenti | G06F 16/955 340/10.1 |
| 2014/0074496 A1* | 3/2014 | Tsai | G16H 20/13 705/2 |
| 2014/0317082 A1* | 10/2014 | Archuleta | G06F 16/9554 709/204 |
| 2017/0103560 A1 | 4/2017 | Kraft et al. | |

FOREIGN PATENT DOCUMENTS

| | | | |
|---|---|---|---|
| WO | WO-2008144575 A2 * | 11/2008 | ......... A61B 5/14532 |
| WO | WO 2019/096875 | 5/2019 | |
| WO | WO 2021/260006 | 12/2021 | |

OTHER PUBLICATIONS

International Search Report and Written Opinion in International Appln. No. PCT/EP2021/067148, mailed on Oct. 21, 2021, 17 pages.

Signer, "Fundamental Concepts for Interactive Paper and Cross-Media Information Spaces," Dissertation for the Degree of Doctor of Technical Sciences, Swiss Federal Institute of Technology Zurich, 2005, retrieved on Jan. 3, 2023, retrieved from URL <http://e-collection.library.ethz.ch/eserv/eth:28630/eth-28630.02.pdf>, 273 pages.

Uluyol et al., "Integrating mobile multimedia into textbooks: 2D barcodes," Computers &Education, Dec. 2012, 59(4):1192-1198.

* cited by examiner

SYSTEM AND METHOD FOR PROVIDING ADDITIONAL INFORMATION TO A USER OF AN INJECTION DEVICE

CROSS REFERENCE TO RELATED APPLICATIONS

The present application is the national stage entry of International Patent Application No. PCT/EP2021/067148, filed on Jun. 23, 2021, and claims priority to Application No. EP 20315319.2, filed on Jun. 25, 2020, the disclosures of which are incorporated herein by reference.

TECHNICAL FIELD

The present disclosure relates to a monitoring system including a first device and a second device and to a method of operating the monitoring system.

BACKGROUND

A variety of diseases exist that require regular treatment by injection of a medicament. Such injections can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a reusable pen may be used. A reusable pen allows replacement of an empty medicament cartridge by a new one. Either pen may come with a set of one-way needles that are replaced before each use. The insulin dose to be injected can then for instance be manually selected at the insulin pen by turning a dosage dial and observing the actual dose from a dosage window of the insulin pen. The dose is then injected by inserting the needle into a suited skin portion and pressing an injection button of the insulin pen. In reusable devices, once the cartridge is empty or the medicament contained in the cartridge is past its expiration date, the cartridge must be replaced.

The user must be thus familiar with a number of operations to be performed with the injection device. The user may, however, feel not confident performing the various tasks and operations based on the written instructions provided in instructions for use in the form of a leaflet enclosed with the injection device. Alternatively or in addition, the user may prefer searching for and reviewing additional information.

Thus, there is a need for improvement in tools enabling the user to find verified information and support in a form that suits the user.

SUMMARY

In a first aspect of the disclosure, a system for providing additional information to a user of an injection device is provided. The system comprises an injection device, a user device and instructions for use of the injection device, the user device comprises a processor, a memory, at least one wireless module and at least one camera, the instructions for use comprising at least one tag, wherein the tag is associated with the instructions for use or with a section or a subsection of the instructions for use, wherein the memory of the user device stores instructions which, when executed by the processor, cause the user device to: scan, using the camera and/or the wireless module, the tag; identify the instructions for use or the section of the instructions for use which the tag is associated with; based on the identification, provide the user with additional information on the particular instructions for use or the particular section of the instructions for use.

In embodiments of the first aspect of the disclosure, one or more of the following features may be used, alone or in combination:
- the user device is a mobile phone or a tablet;
- the tag is a data matrix code;
- the tag is one of the following: a QR code, a barcode, a PDF417 code, Semacode;
- the tag is a RFID tag;
- the tag is a NFC tag;
- the instructions for use are provided as a foldable sheet onto which written information is printed, or as a booklet containing written printed information;
- the tag contains additional information relevant to information provided in the instructions for use;
- the tag contains a command to be executed by the processor of the user device;
- the tag contains a Uniformed Resource Locator (URL) leading to a website which contains additional information relevant to information provided in the instructions for use;
- the tag is one of the following: a unique picture, a unique color or colors, or a unique number;
- the user device is adapted to: scan, using the camera, the printed text in the instructions for use; recognize the characters in the scanned printed text in the instructions for use; identify the section or subsection of the scanned instructions for use based on the recognized text; and provide the user additional information based on the recognized text and/or the recognized section or subsection of the instructions for use;
- the user device is adapted to: scan, using the camera, the printed text in the instructions for use; recognize the design of the section of subsection of the scanned instructions for use; identify the section or subsection of the scanned instructions for use based on the recognized design; and provide the user additional information based on the recognized design and/or the recognized section or subsection of the instructions for use.

In a second aspect of the present disclosure, a method of providing additional information to a user of an injection device is provided. The method comprises: providing instructions for use, wherein the instructions for use comprise at least one tag, wherein the tag is associated with the instructions for use or with a section or a subsection of the instructions for use; scanning, using a camera and/or a wireless module of a user device, the tag; identifying the instructions for use or the section of the instructions for use which the tag is associated with; based on the identification, providing the user with additional information on the particular instructions for use or the particular section of the instructions for use.

In embodiments of the second aspect of the disclosure, one or more of the following features or steps may be used, alone or in combination:
- the tag contains a command to be executed by the processor of the user device and wherein the method further comprises: identifying the command, and executing the command;
- the method further comprises requesting confirmation from the user before executing the command;
- the method further comprises, after identifying the instructions for use or the section of the instructions for use which the tag is associated with: displaying a "Help" button; receiving actuation of the button; and providing help and/or additional information in response to receiving actuation of the button.

In a third aspect of the present disclosure, a user device capable of providing a personalized animation or video content is provided. The user device comprises a processor, a memory, at least one wireless module and at least one camera, wherein the memory of the user device stores instructions which, when executed by the processor, cause the user device to: capture, using the camera, an image of the user; process, using the processor, the image of the user to determine at least one user's characteristic; and generate, using the processor, video or animation content, taking into account the at least one user's characteristic determined from the image of the user.

In embodiments of the third aspect of the disclosure, one or more of the following features may be used, alone or in combination:
  the user device is configured to collect the one or more of the user's characteristics from the user's accounts;
  the user device is configured to collect at least one of the following data about the user: gender, age, city or country of origin, city or country of residence, preferred language, body mass index, the race or ethnicity;
  the user device is configured to estimate the user's body mass index based on the shape and width of the user's face, neck, chin and cheeks;
  the user device is configured to recognize the user's gender based on presence or absence of facial hair or the size and shape of the user's nose, chin, jaw or eyebrows;
  the user device is configured to create a provisional set of characteristics and subsequently request the user to confirm the one or more user's characteristics.
  the user device is configured to allow the user to set or adjust the one or more user's characteristics.

In a fourth aspect of the present disclosure, a method of providing a personalized video or animation content using a user device is provided. The user device comprises a processor, a memory, at least one wireless module and at least one camera, and the method comprises: capturing, using the camera of the user device, an image of the user; processing, using the processor of the user device, the image of the user to determine at least one user's characteristic; generating, using the processor of the user device, video or animation content, taking into account the at least one user's characteristic determined from the image of the user.

In embodiments of the fourth aspect of the disclosure, one or more of the following features or steps may be used, alone or in combination:
  one or more of the user's characteristics from the user's accounts is collected from the user's accounts;
  at least one of the following data about the user is collected: gender, age, city or country of origin, city or country of residence, preferred language, body mass index, the race or ethnicity;
  the user's body mass index is estimated based on the shape and width of the user's face, neck, chin and cheeks;
  the user's gender is recognized based on presence or absence of facial hair or the size and shape of the user's nose, chin, jaw or eyebrows;
  a provisional set of characteristics is created and the user is subsequently requested to confirm the one or more user's characteristics;
  the user is allowed to set or adjust the one or more user's characteristics.

BRIEF DESCRIPTION OF THE FIGURES

In the Figures.

DETAILED DESCRIPTION

In the following, embodiments of the present disclosure will be described with reference to a reusable insulin injection device. The present disclosure is however not limited to such application and may equally well be deployed with injection devices that eject other medicaments or with other types of medicament administration devices. The present disclosure is also not limited to a reusable injection device and may equally well be employed with a disposable injection device.

Figure 1:
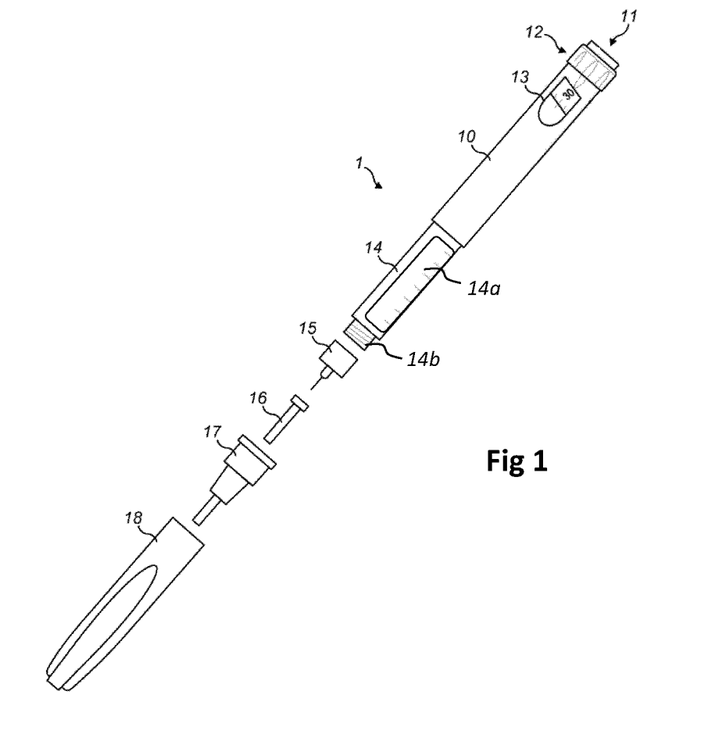
FIG. 1 is a perspective view of a pen-type drug delivery device.

FIG. 1 is an exploded view of an injection device 1, which may for instance represent Sanofi's AllStar Pro™ insulin injection pen.

The injection device 1 of FIG. 1 is a reusable injection pen that comprises a housing 10 and contains an insulin container 14. The insulin container 14 may contain a drug window 14a through which the drug may be viewed. The insulin container 14 may comprise a threaded connector to which a needle 15 can be affixed. The needle 15 is protected by an inner needle cap 16 and an outer needle cap 17, which in turn can be covered by a cap 18.

An insulin dose to be ejected from the injection device 1 can be selected by turning the dosage dial 12. The selected dose is then displayed via dosage window 13, for instance in multiples of so-called International Units (IU), wherein one IU is the biological equivalent of about 45.5 micrograms of pure crystalline insulin (1/22 mg). An example of a selected dose displayed in dosage window 13 may, for instance, be 30 IUs, as shown in FIG. 1. It should be noted that the selected dose may equally well be displayed differently, for instance, by means of an electronic display.

Turning the dosage dial 12 causes a mechanical clicker to provide haptic and acoustic feedback to a user. The numbers displayed in dosage window 13 are present on a sleeve by printing and the sleeve is contained in housing 10 and mechanically interacts with a piston in insulin container 14. When needle 15 is stuck into a skin portion of a patient and then injection button 11 is pushed, the insulin dose displayed in dosage window 13 will be ejected from the injection device 1. When the needle 15 of the injection device 1 remains for a certain time in the skin portion after the injection button 11 is pushed, a high percentage of the dose is actually injected into the patient's body. Ejection of the insulin dose also causes a mechanical click sound, which is different from the sounds produced when using dosage dial 12.

The injection device 1 may be used for several injection processes until either insulin container 14 is empty or the expiration date of the injection device 1 is reached (e.g., 28 days after the first use). The injection device 1 can then be refilled, or the insulin container 14 may be replaced. The replacement may be effected e.g., by removing the cap 18, unscrewing the insulin container 14, removing the cartridge, inserting a fresh cartridge, and replacing the insulin container 14.

Figure 2:
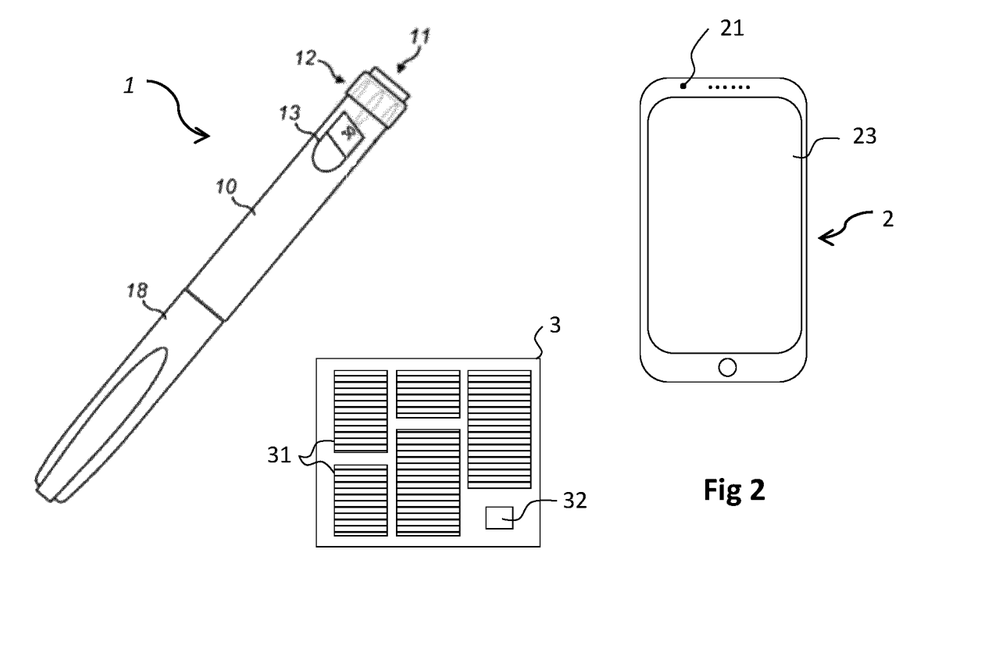
FIG. 2 shows a system of a pen-type drug delivery device, written instructions for use, and a user device.

FIG. 2 shows a system comprising the injection device 1, a user device 2 and instructions for use 3.

The injection device 1 may be for example as described above. The injection device 1 may be any other suitable injection device.

The user device 2 may be for example an electronic device, such as mobile phone or tablet (more generally, a mobile device). The user device 2 may be a desktop PC, a laptop, or a tablet. The user device 2 comprises a screen 23. The screen 23 may be e.g., a touch screen. At least one camera 21 may be associated with the user device 2. The camera 21 may be integral part of the user device 2. The camera 21 may be a front camera or a back camera. The camera 21 may be an external camera, such as a webcam.

The instructions for use 3 may be provided e.g., as a foldable sheet onto which written information 31 is printed. The sheet may be e.g., a paper sheet. The instructions for use 3 may be provided e.g., as a booklet containing written printed information 31. The information provided in the instructions for use 3 may be on the drug contained in the injection device 1, the injection device 1, the handling and operation of the injection device 1, the dosing of the drug contained in the injection device 1, the medical condition the drug has been prescribed for, any side effects of the drug, etc. In an embodiment, the instructions for use 3 contain all information prescribed by a regulatory body.

In addition to written information 31, the instructions for use 3 may comprise at least one tag 32. The user device 2 may be configured to recognize the tag 32. The tag 32 may be associated with particular instructions for use 3 (e.g., instructions for use of a given type of injection device 1). The tag 32 may be associated with particular section of the instructions for use 3. The tag 32 may be e.g., a QR code 32a (shown schematically in FIG. 3a), a barcode, an Aztec code, a Snowflake Code, a PDF417 code, a Semacode, a High Capacity Color Barcode, or any other suitable data matrix code. The tag 32 may be a RFID tag 32b (shown schematically in FIG. 3b). The tag 32 may be a unique picture, a unique color or colors, or a unique number. Unique in this context may mean that the same instructions for use 3 do not contain two same or similar elements of the same type (e.g., the same picture associated with two different subsections of the instructions for use 3). Unique in this context may mean that two different instructions for use 3 provided for two different types of injection device do not contain the same or similar elements of the same type (e.g., the same picture associated with two different instructions for use 3).

Figure 3A:
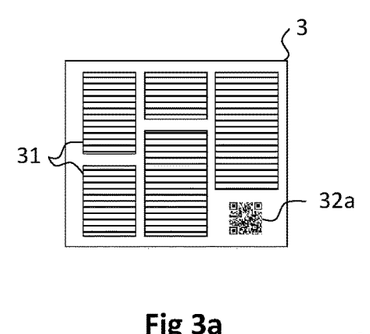
FIGS. 3a-3c are schematic representation of instructions for use of an injection device.
Figure 3B:
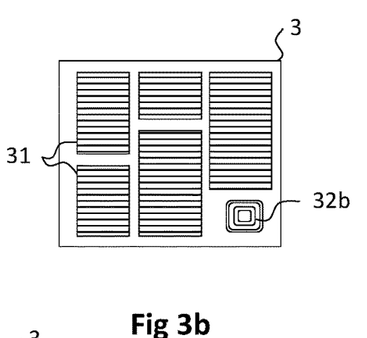

The user device 2 may be adapted to scan, sense, or otherwise recognize the tag 32. For example, if the tag 32 is a QR code 32a or alternative data matrix code, the user device 2 may be provided with suitable software (such as an app) which is adapted to capture an image of the tag 32 with a camera 21 of the user device and decode the tag 32 (retrieve the information provided in the tag 32). For example, if the tag 32 is a RFID tag 32b, the user device 2 may use a wireless module 22 (such as a RFID module) to read the tag 32b.

In an embodiment, each section and/or each subsection of the instructions for use 3 has a tag 32 associated with that section. In an embodiment, only certain sections may have a tag 32 associated with them. In an embodiment, there may be only one tag 32 associated with the instructions for use 3. Each section and/or subsection of the instructions for use 3 may have a unique tag 32 associated with it. The association of the tag(s) 32 and the section(s) or subsection(s) of the instructions for use 3 may be stored by the user device 2 in its memory 25.

In an embodiment, the tag 32 contains additional information relevant to the information provided in the instructions for use 3. In an embodiment, the tag 32 may contain a command to be executed by the user device 2. For example, the tag 32 may provide a Uniformed Resource Locator (URL) leading to a website which contains additional information relevant to the information provided in the instructions for use 3. For example, the tag 32 may provide a command to retrieve additional information relevant to the information provided in the instructions for use 3 from the memory 25 of the user device 2 and provide this additional information to the user.

For example, the additional information may contain further details on the information given in the instructions for use 3. For example, the website and/or the additional information retrieved from the memory 25 of the user device 2 may contain additional information in the form of picture instructions and/or a video explaining a particular task which is to be completed with the injection device 1. Tasks may involve for example preparing for injecting the drug, injecting the drug, removing and/or replacing an empty cartridge, removing and/or replacing a used needle, checking the expiration date and/or quality of a medicament contained in the cartridge, and the like.

In an example embodiment (shown in FIG. 3c), the instructions for use 3 may contain a plurality of subsections 311-313. Among the plurality of subsections, there may be for example a subsection on dialling the correct dose of the drug 311, a subsection on injecting the dialled dose 312, and a subsection on replacing an empty cartridge 313. Each of these subsections may have a distinct tag 321-323 associated with them. The tags 321-323 may be e.g., as described above (a data matrix tag, a RFID tag, or any other suitable tag). Each of the tags 321-323 may contain additional information and/or a command to be executed by the user device 2. For example, the tags 321-323 may contain a URL leading to a website containing a video showing the correct process of executing the respective procedure described in the sections 311-313. Thus, when each of the tags 321-323 is scanned by the user device 2, the user device may open the respective website and show the user the respective video.

Figure 3C:
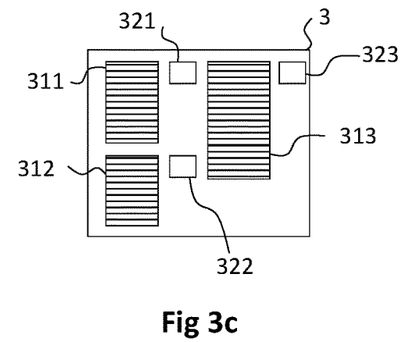

Alternatively or in addition, the URL may lead to a text-based website providing additional information, to additional picture-based user instructions, or the like. The tags 321-323 may also contain a command for the user device 2 to retrieve additional information from elsewhere, e.g., the memory 25 of the user device 2.

In an embodiment, after scanning the tag 32, the user device 2 may request the user to confirm the user's request to access additional information. This may be done e.g., by displaying, on the screen 23 of the user device 2, a suitable question (e.g., "Do you wish to view an additional information for this section?") and a choice of "Yes" and "No" soft buttons, to be touched by the user. Alternatively or in addition, the user device may, using the screen 23, display a "Help" button. Upon actuating, e.g., touching, the "Help" button, the user may be provided with the additional information, e.g., a video showing a correct handling of the injection device 1 and/or performing a specific task, as described above.

Providing the tag(s) 32 in the instructions for use 3 may help in making sure that the additional information is verified, authorised and up-to-date. For example, by being provided a video made by the manufacturer of the injection device 1, a regulatory body, a health care professional or a verified user group, the user may be motivated to review and follow this video, thus diminishing the user's need for searching for further information on their own and possibly reviewing irrelevant information (such as information which is related to a different injection device than the user owns, information which is outdated, inaccurate, fake or otherwise faulty, etc.).

Alternatively or in addition, the user device 2 may be adapted to recognize the instructions for use 3 and/or a particular section or subsection 31 of the instructions for use 3 based on the text present in the instructions for use 3. For example, after capturing an image of the instructions for use 3, the user device 2 may be configured to recognize the characters in the printed text (using e.g., optical character recognition, or OCR), and offer the user additional information as described above in response to recognizing the text. For example, the user device 2 may recognize a particular subsection of the instructions for use 3, for example based on a particular heading, and in response provide the user with the option of viewing the additional information, as described above.

Alternatively or in addition, the user device 2 may be adapted to recognize the instructions for use 3 and/or a particular section or subsection 31 of the instructions for use 3 based on the design of the instructions for use 3. For example, the user device 2 may recognize any combination of the following: layout of the instructions for use 3, colors used in the instructions for use 3, pictures and diagrams provided in the instructions for use 3, fonts, size of the text and/or the headings, presence or absence of bold text, underlined text and/or italics, presence or absence of particular headings and the like). In response to recognizing these features, the user device 2 may provide the user with the option of viewing the additional information related to a given subsection, as described above.

Figure 4:
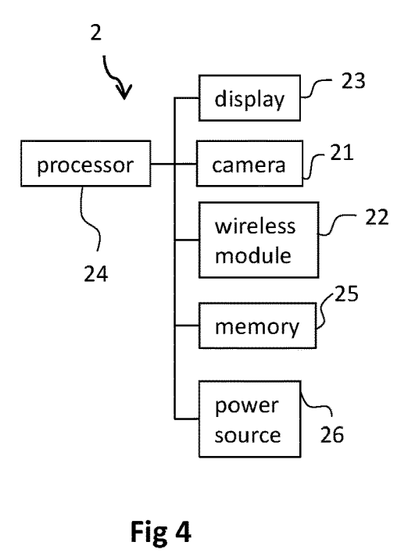
FIG. 4 is a schematic representation of a user device.

A schematic view of the user device 2 is provided in FIG. 4. The user device 2 may comprise a processor 24. The user device 2 may comprise a camera 21, which may be a front camera or a back camera. There may be more than one camera 21, or more than one camera 21 of each type, associated with the user device 2. The user device 2 may comprise a wireless module 22. The wireless module 22 may be, e.g., an RFID module, a NFC module, or the like. The user device 2 may comprise a display 23, for example a screen or a touch screen. Any other suitable display may be provided. In case the display 23 is not a touch screen, the user device 2 may be provided with a button- or key-based input device (not shown). The user device 2 may comprise a memory 25. The memory 25 stores suitable software (e.g., an app) configured to identify/recognize the instructions for use 3 and provide additional information, as described above. The user device 2 may further comprise a battery or other suitable power source 26.

Figure 5:
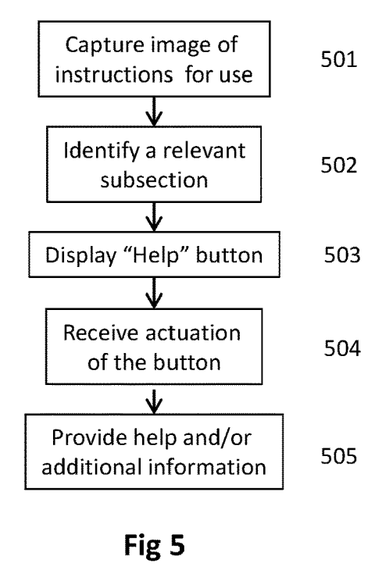
FIGS. 5-7 show example methods executed by the user device.
Figure 6:
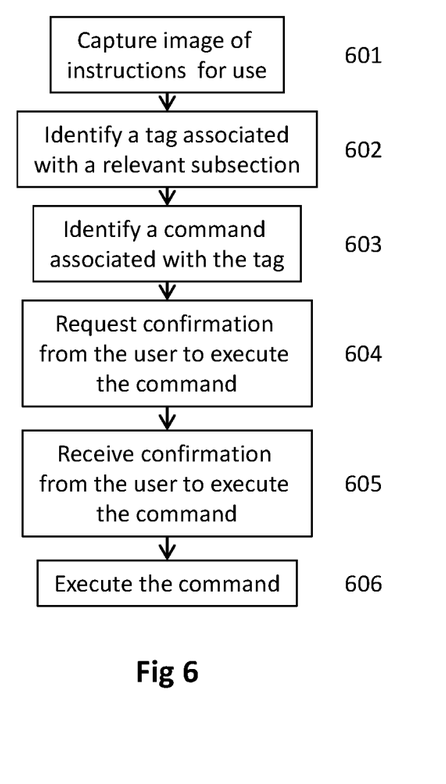
Figure 7:
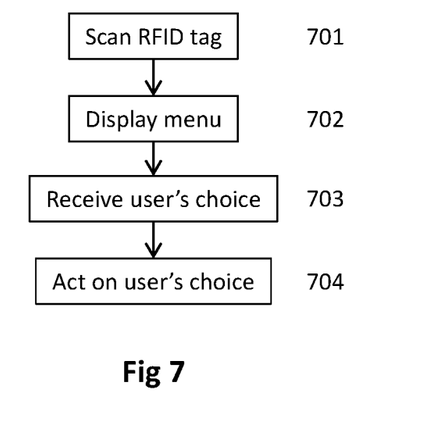

In some embodiments, the user device 2 is configured to perform methods of providing additional information to the user. Example methods are shown in FIGS. 5 to 8. The methods of FIGS. 5-8 are shown as exemplary only; it will be understood that the steps can be combined as appropriate. FIGS. 5-7 show methods of providing additional information to the user, using the screen 23 of the user device 2. The methods of FIGS. 5-6 utilize the camera 21 of the user device 2. The camera 21 may be a front camera or a rear camera. The method of FIG. 7 utilizes a wireless module 22, e.g., a RFID module or a NFC module of the user device 2.

In the method of FIG. 5, the camera 21 of the user device 2 is used to capture image of the instructions for use 3 (step 501). The image is processed by the user device 2 (e.g., using a processor 24 and a suitable app provided in the memory 25 of the user device 2).

A relevant subsection of the instructions for use 3 is identified in step 502, for example based on OCR and/or design features, as described above.

In step 503, the user device 2, using the screen 23, displays a "Help" button. The "Help" button may be a soft button displayed on a touch screen 23. Alternatively, the "Help" button may be actuated in any other suitable way (e.g., using a desktop computer keyboard and mouse).

Once the user actuates the "Help" button and the user device 2 receives this actuation (step 504), the user device 2 accesses additional information and shows the additional information to the user (step 505). The additional information may be e.g., a video, animation or picture tutorial showing a correct handling of the injection device described in the relevant subsection of the instructions for use 3. The additional information may be further reading material related to the relevant subsection of the instructions for use 3.

FIG. 6 shows another method of providing additional information to the user. In step 601, the camera 21 of the user device 2 is used to capture an image of the instructions for use 3. The image is then processed as described above in connection with method of FIG. 5.

A tag 32 associated with a relevant subsection of the instructions for use 3 is identified by the user device 2, e.g., using a suitable app (step 602).

Based on the identification of the tag 32 in step 602, a command associated with the tag is identified (step 603). For example, the tag 32 may contain a URL of a webpage, and the associated command may be opening the webpage. For example, the tag 32 may comprise a command for the user device 2 to retrieve specific information from the memory 25 of the user device 2 and/or from an app stored in the memory 25 of the user device 2.

In step 604, the user device 2 may request a user's confirmation to execute the identified command. The user device 2 may use the screen 23 to display a request for confirmation, e.g., in a form of a soft button to be actuated by the user.

Upon receiving, in step 605, a confirmation from the user that the command is to be executed, the command is executed in step 606. For example, the URL is searched for, a video-, audio- and/or text-based additional information is accessed, and the like.

FIG. 7 shows another method of providing additional information to the user. In step 701, the user device 2, which has a RFID module 22 and is RFID-enabled, scans the RFID tag 32 provided in the instructions for use 3. The tag 32 prompts the user device 2 to display a menu (step 702), providing the user with choice of actions or commands to be executed. For example, the menu may provide the user with a choice between watching different videos, reading different pieces of further reading material, reviewing picture- or animation-based instructions, and the like.

Once the user makes their choice, the choice is received by the user device 2 (step 703), and then the associated action is performed and/or the associated command is executed.

The steps of the methods of FIGS. 5-7 may be combined to create a method not shown in the Figs. For example, after capturing an image of the instructions for use 3 and identifying a relevant subsection (steps 501 and 502 of FIG. 5), the user device 2 may proceed to display a menu (as described in connection with FIG. 7, step 702 and subsequent). For example, after scanning the RFID tag 32 (step 701 in FIG. 7), the user device 2 may continue with identifying a command associated with the tag 32 (steps 602-606 of FIG. 6), or may display a help button (steps 502-505 of FIG. 5). For example, after capturing an image of instructions for use 3 and identifying a tag associated with a relevant subsection (steps 601 and 602 of FIG. 6), the user device 2 may proceed to displaying a "Help" button (steps 503-505) or menu (steps 702-704 of FIG. 7).

In other words, the user device 2 may be configured to identify instructions for use 3, one or more of sections or subsections of instructions for use 3, or a tag 32 associated with instructions for use 3 or its section(s) or subsection(s). The user device 2 may then proceed to offer additional help to the user and/or execute commands associated with the tag(s) 32 and/or provide the user with menu of options and execute the chosen option.

Additional information available to the user in the form of video or animated content may show an avatar representing the user, performing the various tasks. The video or animated content may be provided from the point of view of this avatar, or it may closely follow the avatar.

It may be desirable to provide an avatar which the user may identify with. For example, a female user may prefer to watch a female avatar. As another example, a user identifying with a particular ethnic or religious background may prefer an avatar having the same ethnic or religious background, etc. The user may be able to adjust the avatar's skin tone. For example, the user may be able to pick the avatar's skin tone from several different options, for example from a drop-down menu. Alternatively or in addition, the avatar's gender, skin tone and other characteristics may be based on a captured image of the user (as described below).

The user may prefer it if the avatar conforms to certain cultural norms. For example, if the user's culture considers showing one's bare arms or legs as unacceptable, the user may prefer an avatar dressed such that the avatar's arms and legs are fully covered. Alternatively or in addition, if the user's culture considers showing bare skin unacceptable, the avatar may not show bare skin at all. In that case, when the avatar demonstrates a correct injection technique into a portion of bare skin, that portion of bare skin may be shown in one or more following ways: covered except for a very small area needed for the injection, pixelated, in abstract representation such as relief or in pastel. Similarly, if the user's culture considers showing certain portions of the user's body (e.g., a belly button or thighs) unacceptable, the avatar may not show these body parts, or show them pixelated or in abstract representation, as described above.

Alternatively or in addition, the user may prefer to watch content in which the avatar's surroundings are familiar to the user (e.g., the furniture is such as is customary in the user's region, the contents of the avatar's fridge is similar to the contents of the user's fridge, etc.).

If the user is provided with content which takes into account the personal and cultural preference (a suitable avatar, suitable surroundings etc.), the user may pay more attention to the relevant content of the video or animation. For example, the user may pay attention to instructions for use of an injection device and demonstration of the use of the injection device 1 by the avatar, and less attention to the background and/or less relevant information such as the avatar's clothing, which may be perceived inappropriate or alien, or the avatar's surroundings, which may be considered more interesting by the user than the injection device being demonstrated.

To be able to predict the user's preferences in this aspect, the user device 2, preferably with the user's prior consent, collects certain information about the user. Among the collected information may be user's gender, age, city or country of origin, city or country of residence, language, body mass index, the race or ethnicity the user identifies with, and the like. With this information, the user device 2 may be able to set the avatar and/or the avatar's surroundings according to the user's culture, taste and/or preference.

Figure 8:
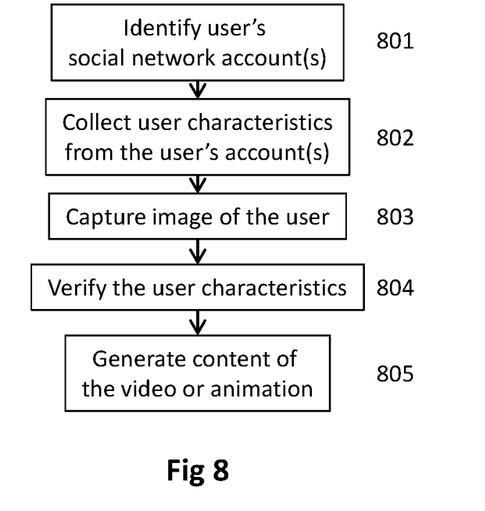
FIG. 8 shows an example method of determining the user's characteristics.

An example method for determining a suitable avatar and/or suitable surroundings of the avatar is shown in FIG. 8.

In step 801, the user device 2 may identify one or more of the user's social network accounts. For example, the user may be requested to input their email or social network or other account details.

In step 802, information is retrieved from the user's social network account(s). For example, the user device 2 may collect information such as name, age, city or country of residence, or preferred language. The information obtained may be stored in the user device 2, for example in a memory 25 of the user device.

In step 803, the user may be requested to capture an image of themselves. The user device 2 may contain suitable software which is configured to recognize certain features. For example, based on the shape, width and other parameters of the user's face, neck, chin and cheeks, the user device 2 may be able to estimate the user's body mass index. Based on presence or absence of facial hair and the size and shape of some of the facial features (such as the user's nose, chin, jaw or eyebrows), the user device 2 may be able to recognize the user's gender. Alternatively or in addition, user's gender, age and/or other characteristics may be input directly by the user, outsourced from an external source such as social network or other user account, or both.

To identify the various characteristics of the user, the user device 2 may be able to capture, recognize a process one or more of the following parameters, alone or in combination:
- the user's skin tone, tanned appearance etc., which could be indicative of the user's ethnic background, general health, specific health issues, wellbeing or lifestyle;
- color, length, texture, volume and/or other characteristics of the user's hair, which could be indicative of the user's ethnic background, gender, age, general health, specific health issues, wellbeing or lifestyle;
- gloss of skin and hair, which could be indicative of the user's lifestyle choices (for example, groomed appearance or more 'casual' appearance);
- the user having a double chin, which could be indicative of the user being overweight;
- the user having hanging eyelids and corners of the mouth, which could be indicative of the user's wellbeing;
- appearance of a portion of the user's neck (throat), which could indicate the user is overweight;
- the appearance of the user's hands and/or the appearance of the skin of the user's hands, which can be indicative of the user's age and wellbeing;
- the user's hand movements, which can be indicative of the user's age and wellbeing.

In an optional step 804, the user device 2 may request the user to confirm one or more captured or derived characteristics. For this, the user device 2 may create a provisional set of characteristics (e.g., assume that the user is of particular gender and identifies with a particular race or ethnicity) and request the user to confirm.

Alternatively, instead of capturing an image of the user (step 803), the user may be asked to input the data about themselves (not shown). For example, the user may be requested to indicate whether they are male or female, state their body mass index, and pick their preferred race, ethnicity or religion.

Once the set of the user's features is finalized, the content of video or animation is generated. The user's characteristics are used to generate an appropriate avatar (e.g., an avatar of particular gender, dressed in a particular way, surrounded by particular home furnishings and equipment).

The user may be provided with a possibility to change the avatar's characteristics. For example, if the user is identified by the user device 2 as being of a particular gender, but the user identifies with a different gender, the user may be able to switch the avatar to a different gender.

Alternatively or in addition, the user may be provided with a range of lifestyle choices. For example, if the user follows a specific diet (e.g., vegetarian, vegan or paleo diet), the user may be able to indicate this to the user device 2 and change the contents of the fridge shown in the video.

The identification of the user's preferred language and cultural background may influence other settings of the content, such as the way information is presented. For example, menu options, layout and other properties may be influenced by the user's expectations. For example, the color scheme may be set based on the user's cultural preferences (e.g., a Chinese user may prefer red color scheme, a Russian user may prefer gold color scheme, and a Western user may prefer white, grey or cream color scheme).

As another example, the presentation of the information, menu and/or navigation may be based e.g., on the level of the user's training: a user who is not yet trained may be presented with simple, more intuitive navigation, while an experienced user may see a more advanced version of the navigation, allowing access to advanced settings etc.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codeable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g., a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N—(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g., a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof.

An example drug delivery device may involve a needle-based injection system as described in Table 1 of section 5.2 of ISO 11608-1:2014(E). As described in ISO 11608-1:2014 (E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The invention claimed is:

1. A system for providing additional information to a user of an injection device, the system comprising:
   a user device, the user device comprising a processor, a memory, at least one wireless module, and at least one camera; and
   printed instructions for use of the injection device, the printed instructions for use being in the form of a paper sheet or booklet and comprising at least one tag, wherein the at least one tag is associated with the printed instructions for use or a section or a subsection of the printed instructions for use,
   wherein the memory of the user device stores instructions which, when executed by the processor, cause the user device to:
     scan, using at least one of the camera or the at least one wireless module, the at least one tag; and
     identify the printed instructions for use or a corresponding section or subsection of the printed instructions for use with which the at least one tag is associated,
   wherein the at least one tag contains a command to be executed by the processor of the user device, wherein the command is configured to cause the user device to retrieve additional information relevant to the information provided in the printed instructions for use or the section or subsection of the instructions for use, and wherein the additional information comprises picture instructions and/or a video,
   wherein the user device is adapted to:
     scan, using the camera, a printed text in the printed instruction for use;
     recognize (i) characters or (ii) a design of a section or subsection of the scanned printed text in the printed instructions for use; and
     in response to recognizing the characters, identify a corresponding section or subsection of the printed instructions for use based on the recognized characters, and provide the user with at least one of (i) the additional information based on the recognized characters or (ii) the corresponding section or subsection of the printed instructions for use, or
     in response to recognizing the design, identify a corresponding section or subsection of the printed instructions for use based on the recognized design; and provide the user with at least one of (i) the additional information based on the recognized design or (ii) the corresponding section or subsection of the printed instructions for use.

2. The system of claim 1, wherein the at least one tag is one of a data matrix code, a QR code, a barcode, a PDF417 code, a Semacode, an RFID tag, or an NFC tag.

3. The system of claim 1, wherein the at least one tag is one of a unique picture, a unique color or colors, or a unique number.

4. A method of providing additional information to a user of an injection device, comprising:
   scanning, using at least one of a camera or a wireless module of a user device, a tag included in printed instructions for use, wherein the tag is associated with the printed instructions for use or a corresponding section or subsection of the printed instructions for use, wherein the printed instructions for use is in the form of a paper sheet or booklet and comprise at least one tag;
   identifying the printed instructions for use or the corresponding section or subsection of the printed instructions for use with which the tag is associated, wherein the at least one tag contains a command to be executed by the processor of the user device; and
   executing the command to retrieve additional information relevant to the information provided in the printed instructions for use or the corresponding section or subsection of the instructions for use, and wherein the additional information comprises picture instructions and/or a video,
   wherein the method further comprises:
     scanning, using the camera, a printed text in the printed instructions for use;
     recognizing (i) characters or (ii) a design of a section or subsection in the scanned printed text in the printed instructions for use; and
     in response to recognizing the characters, identifying a corresponding section or subsection of the printed instructions for use based on the recognized characters, and providing the user with at least one of (i) the additional information based on the recognized characters or (ii) the corresponding section or subsection of the printed instructions for use, or
     in response to recognizing the design, identifying a corresponding section or subsection of the printed instructions for use based on the recognized design, and providing the user with at least one of (i) the additional information based on the recognized design or (ii) the corresponding section or subsection of the printed instructions for use.

5. The method of claim 4, wherein the method further comprises requesting confirmation from the user before executing the command.

6. The method of claim 4, wherein the method further comprises, after identifying the printed instructions for use or the corresponding section or subsection of the printed instructions for use with which the tag is associated:
   displaying a "Help" button;
   receiving an actuation of the "Help" button; and
   providing help and/or additional information in response to receiving the actuation of the "Help" button.

* * * * *